US007113278B2

(12) United States Patent
Choo et al.

(10) Patent No.: US 7,113,278 B2
(45) Date of Patent: Sep. 26, 2006

(54) LIQUID CRYSTAL PROCESS DEFECT INSPECTION APPARATUS AND INSPECTION METHOD

(75) Inventors: Dae-Ho Choo, Suwon (KR); Min-Young Won, Kunpo (KR); Hyoo-Hak Nam, Suwon (KR); Beak-Keun Jeon, Yongin (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 0 days.

(21) Appl. No.: 10/492,887

(22) PCT Filed: Apr. 22, 2002

(86) PCT No.: PCT/KR02/00738

§ 371 (c)(1),
(2), (4) Date: Oct. 19, 2004

(87) PCT Pub. No.: WO03/036274

PCT Pub. Date: May 1, 2003

(65) Prior Publication Data

US 2005/0041243 A1 Feb. 24, 2005

(30) Foreign Application Priority Data

Oct. 25, 2001 (KR) ............................ 2001-0065991

(51) Int. Cl.
*G01J 4/00* (2006.01)
(52) U.S. Cl. .................................... 356/364
(58) Field of Classification Search ............. 356/237.1, 356/238.8, 239.1, 239.2, 237.9, 503, 504, 356/495
See application file for complete search history.

(56) References Cited

U.S. PATENT DOCUMENTS 5,392,116 A * 2/1995 Makosch ..................... 356/495
5,481,360 A * 1/1996 Fujita ......................... 356/489
5,781,294 A * 7/1998 Nakata et al. ............... 356/487
6,654,112 B1 * 11/2003 Noguchi et al. ........... 356/237.3

OTHER PUBLICATIONS

PCT International Search Report dated Jun. 25, 2002 corresponding to PCT/KR02/00738.
PCT International Preliminary Examination Report dated Sep. 3, 2003 corresponding to PCT/KR02/00738.

* cited by examiner

*Primary Examiner*—Gregory J. Toatley, Jr.
*Assistant Examiner*—Isiaka O. Akanbi (57) ABSTRACT

The glass substrate test apparatus of the liquid crystal cell process comprises a laser unit for generating a laser beam, a beam shaper and beam collimator for shaping the laser beam emitted from the laser unit so as to have an elongated cross section and parallelizing the shaped laser beam, a photo detector for detecting an intensity of double refraction of the shaped laser beam transmitted over the whole glass substrate, a phase defector for measuring the laser double refraction detected by the photo detector and comparing the measured double refraction with a standard laser double refraction, and a polarizer arranged between the laser unit and the beam shaper or between the beam shaper and the beam collimator for polarizing the laser beam to a parallel ray.

17 Claims, 11 Drawing Sheets

LIQUID CRYSTAL PROCESS DEFECT INSPECTION APPARATUS AND INSPECTION METHOD

BACKGROUND OF THE INVENTION (a) Field of the Invention

The present invention relates to LCD manufacturing, and in particular, to a glass substrate test apparatus and method for optically inspecting defects of an alignment layer before charging liquid crystal into a liquid crystal cell.

(b) Description of the Related Art

Typically, LCD manufacturing includes thin film transistor (TFT) array fabrication, color filter fabrication, and liquid crystal cell fabrication processes.

The TFT fabrication process is similar to the process used to fabricate semiconductor devices where various steps are repeatedly performed, such that it is possible to control a yield by making a decision on proceeding to a next process or reworking the same process by capturing defects immediately after each unit process.

That is, since the basic TFT fabrication process includes the steps of depositing metal and organic material layers and patterning the same, it is possible to inspect defects of the patterns immediately after a photolithography step by measuring electric resistance or through visual analysis.

Accordingly, it is possible to achieve an ideal yield in the TFT fabrication process if the production yield of each step is set to be 100%. In other words, the processing achievement can be electrically and optically determined because the processing of TFT fabrication consists of patterning processes.

The color filter fabrication process includes depositing black matrix and color resin and patterning the deposited layer using photolithography methods, so defect inspection can also be performed after each unit process, as in the TFT fabrication process.

An optical surface analysis rather than an electric analysis is used for inspecting unevenness of the surface or areas where the color resin is badly deposited. Accordingly, there is no difficulty to achieve an ideal yield at each unit process.

On the other hand, there can be two kinds of defect inspection methods in the liquid crystal cell process.

Liquid crystal cell processing consists of two processes, i.e., a glass substrate process including the steps of depositing, curing, rubbing an alignment layer, and assembling the liquid crystal cell; and a process after cutting in unit of crystal cell and before modularizing the crystal cell.

In the second process of liquid crystal cell processing, there is no difficulty to achieve an ideal yield by monitoring the defects at each unit process, because most defect inspection is performed using visual surface analysis at every unit process.

In the first process of liquid crystal cell processing, however, the defects caused while depositing, curing, and rubbing the alignment layer can be optically inspected during the processes. That is, defects such as non-uniformity of the alignment layer caused by pre-cure and cure processes and particles generated in the rubbing process or by other causes during the processes can be inspected using visual surface analysis. However, componential anisotropy can exist on the alignment layer, caused by remaining solvent that does not evaporate because of a difference in curing speed even though the surface of the alignment layer appears even. The componential anisotropy of the alignment layer generates electrostatic alignment anisotropy when charging the liquid crystal material so as to locally destroy alignment on the alignment layer, resulting in stains having different luminance distributions from other areas.

In the conventional inspection method, this kind of stain cannot be detected immediately after the alignment layer cure process. If the stain is detected after the liquid crystal is charged, it is impossible to rework the glass substrate so the yield cannot be improved.

In the alignment layer rubbing process, since uniform furrows having a depth of 50~60 Å are formed, it is impossible to detect defects immediately after the rubbing, but rather an insufficiency of alignment can only be detected by an electrostatic correlation of the rubbing direction and the liquid crystal after the liquid crystal is charged into the liquid crystal cell. Accordingly, in this method, rubbing rework is impossible, and even though the defects are detected, it does not help in improving the yield.

The substantial reason why the defects cannot be detected immediately after each unit process is that the defects of the alignment layer are inspected using optical analysis on the basis of the correlation of the alignment layer and the liquid crystal.

SUMMARY OF THE INVENTION

The present invention has made in an effort to solve the above problem.

It is an object of the present invention to provide a glass substrate test apparatus and method for optically inspecting defects of an alignment layer immediately after each unit process so as to secure a 100% yield in the liquid crystal cell process.

To achieve the above object, the glass substrate test apparatus comprises: a laser unit 1 for generating a laser beam, a beam shaper 3 and beam collimator 5 for shaping the laser beam emitted from the laser unit 1 so as to have an elongated cross section and parallelizing the shaped laser beam, a photo detector 7 for detecting an intensity of double refraction of the shaped laser beam transmitted over the whole glass substrate, a phase detector 13 for comparing the laser double refraction detected by the photo detector 7 and comparing the measured double refraction with a standard laser double refraction, a polarizer arranged between the laser unit and the beam shaper or between the beam shaper and the beam collimator for polarizing the laser beam to a parallel ray.

The beam shaper and beam collimator respectively have shapes of a semi-circular cylinder and are arranged in any pair of convex—convex lenses, convex-concave lenses, concave-convex lenses, and concave—concave lenses. The beam shaper and the beam collimator can be used as a single pair or in multiple pairs. The laser beam from the beam expander is spread by being passed through the beam shaper such that the spread laser beam has an elongated or elliptical cross-section.

The multiple beam shapers and the beam collimators are used for covering a width of the whole glass substrate such that the shaped laser beams are alternately arranged in front and rear rows relative to a progress direction of the glass substrate, and they are arranged having a distance between the shaped laser beams in the same row so as to be overlapped or non-overlapped in two other rows by a predetermined length.

The multiple beam shapers and the beam collimators are used for covering a width of the whole glass substrate such that the shaped laser beams are arranged in a single row and are overlapped or non-overlapped over a predetermined length.

The laser unit, the beam shaper, the beam collimator, and the polarizer are configured in an integral optical system. In the case the beam expander is used, the beam expander is arranged between the laser unit and the beam shaper.

The laser unit, the beam shaper, the beam collimator, and the polarizer are configured in an integral optical system such that the plurality of optical systems are used in consideration of a size of the glass substrate and a length of a shaped laser beam. The beam expander can be excepted.

The photo detector is arranged in a single or as array type identical with the glass substrate for detecting the laser double refraction per unit area.

The beam expander is arranged between the laser unit and the beam shaper and can expand the laser beam by a degree of 1000 times. When the size of the glass substrate is small, the beam expander need not be used.

A sprayer can be arranged between the beam collimator and the glass substrate for magnifying the laser double refraction by spraying water, alcohol, or an organic compound on the glass substrate.

A polarization elastic modulator is arranged between the glass substrate and the photo detector for forming a required wavelength.

The glass substrate test apparatus of the present invention can be used together with a visual test device using any of ultraviolet, infrared, or visible rays for detecting foreign bodies on the surface of the glass substrate 9 in an LCD manufacturing line.

The optical system can adopt a Galvano scanner and an f-θ lens instead of the beam shaper and the beam collimator. The Galvano scanner shapes/spreads the laser beam emitted from the laser unit into multiple directions so as to make a cross section of the spread laser beam be an elongated slit, and the f-θ lens paralyzes the spread laser beam. Multiple optical systems can be used in consideration of the length of the shaped laser beam and the size of the glass substrate.

The glass substrate test apparatus of the present invention can detect the laser double refraction of the glass substrate. The inspection laser beam is arranged above the glass substrate and the photo detector is arranged below the glass substrate.

In the glass substrate test apparatus of the present invention, the photo detector is arranged above the glass substrate and a reflection plate is arranged below the glass substrate such that the laser beam transmitted through the glass substrate is reflected by the reflection plate so as to be directed to the photo detector.

A glass substrate test method in the liquid crystal cell fabricating process according to the present invention comprises the steps of setting standard laser double refraction data to a inspection standard, detecting laser double refraction by projecting a laser beam over the whole glass substrate, comparing the detected laser double refraction with the standard laser double refraction, determining whether or not a double refraction difference is within a utilization range of the class substrate, and judging that the glass substrate has no defects if the double refraction difference is within the utilization range of the glass substrate, or judging that the glass substrate has defects if the double refraction difference is outside the utilization range of the glass substrate and then reworking the glass substrate.

While detecting the laser double refraction, the glass substrate to be tested moves at a speed of the liquid crystal cell process line below a inspection laser beam, or it is positioned below an inspection laser beam without moving.

BRIEF DESCRIPTION OF THE DRAWINGS

The accompanying drawings, which are incorporated in and constitute a part of the specification, illustrate an embodiment of the invention, and together with the description, serve to explain the principles of the invention.

DETAILED DESCRIPTION OF THE PREFERRED EMBODIMENTS

A preferred embodiment of the present invention will be described hereinafter with reference to the accompanying drawings.

Figure 1:
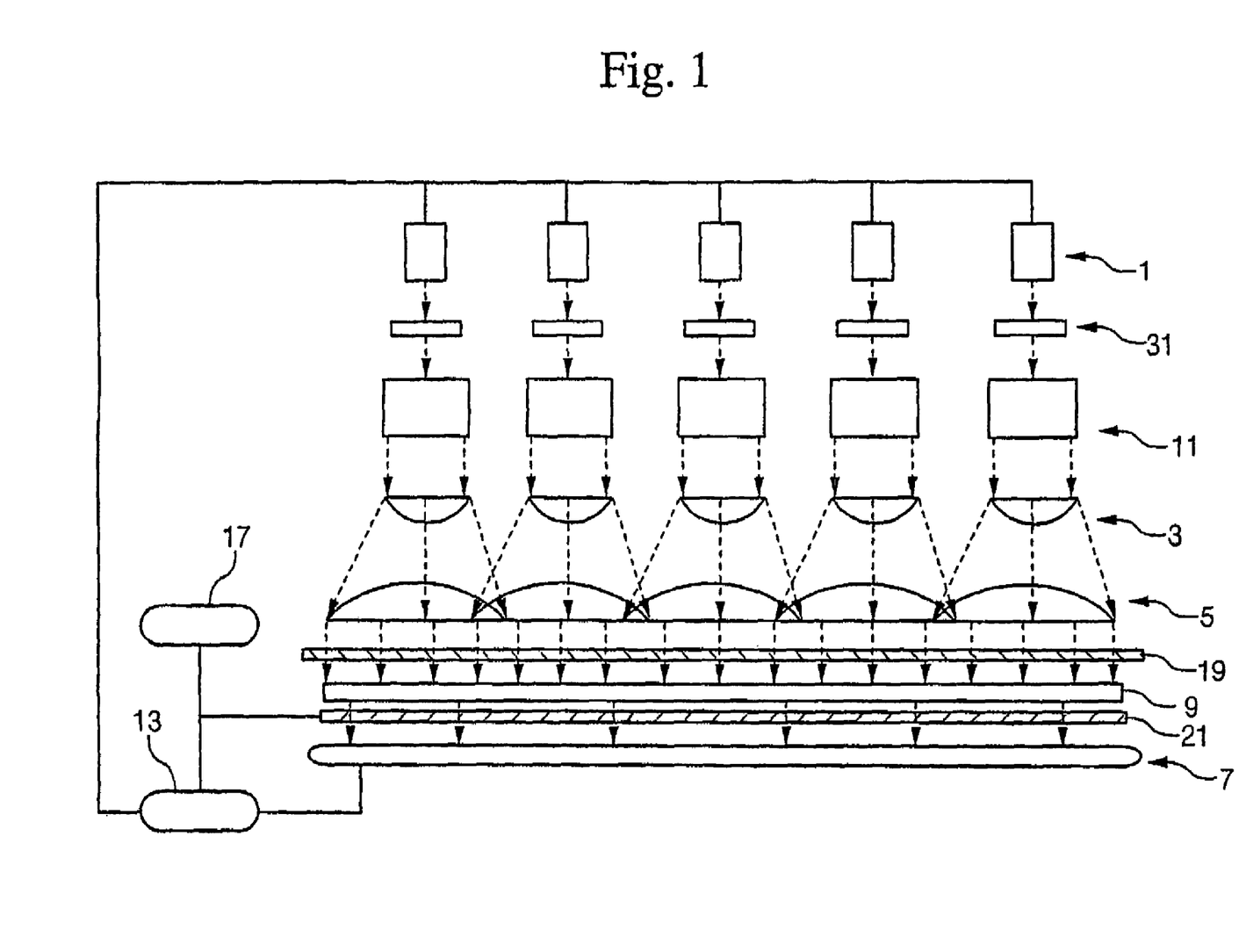
FIG. 1 is a schematic block diagram showing a transmittance-type glass substrate test apparatus according to the present invention.

FIG. 1 is a schematic view showing an apparatus for testing a glass substrate immediately after depositing an alignment layer and/or rubbing the surface of the alignment layer.

In FIG. 1, laser beams are projected to the alignment layer of the glass substrate passing below the laser unit such that the anisotropy of the double refraction of the laser beam caused by the characteristics of the alignment layer is measured so as to be collected as data for determining whether or not the glass substrate has defects.

The laser beam emitted from the laser unit is shaped through an optical system and the shaped laser beam scans the surface of the glass substrate for measuring the double refraction such that it is determined whether or not the glass substrate is defective by comparing the measured double refraction data to a standard double refraction range.

The glass substrate test apparatus comprises a laser unit 1, a beam shaper 3, a beam collimator 5, a photo detector 7, and a polarizer 31.

The laser unit 1 generates a laser beam and projects the same to the glass substrate of the liquid crystal cell so as to be refracted through the glass substrate. The laser beam generated from the laser unit 1 may be one of the He—Ne, Ar, $CO_2$, etc. lasers that do not damage the alignment layer and the liquid crystal. Also, it is possible to use a Hetero Zeemann laser which emits multiple laser beams having different wavelengths.

A plurality of laser units 1 can be used so as to cover a broad scanning range according to the size of the glass substrate to be inspected.

Between the laser unit 1 and the beam shaper 3 a beam expander 11 is arranged. Even though the beam expander 11 can infinitely expand the laser beam emitted from the laser unit 1, it is typically expanded by a degree of 1000 times. Accordingly, when the size of the glass substrate 9 is small, the beam expander 11 need not be used.

In the case the beam expander 11 is used, the laser beam passed through the beam expander 11 is shaped by the beam shaper 3; and in the case the beam expander 11 is not used, the laser beam projected from the laser unit 1 is directly shaped by the beam shaper 3 so as to have an elongated slit form in its cross-section. The shaped laser beam is rendered parallel in the beam collimator 5.

Figure 2:
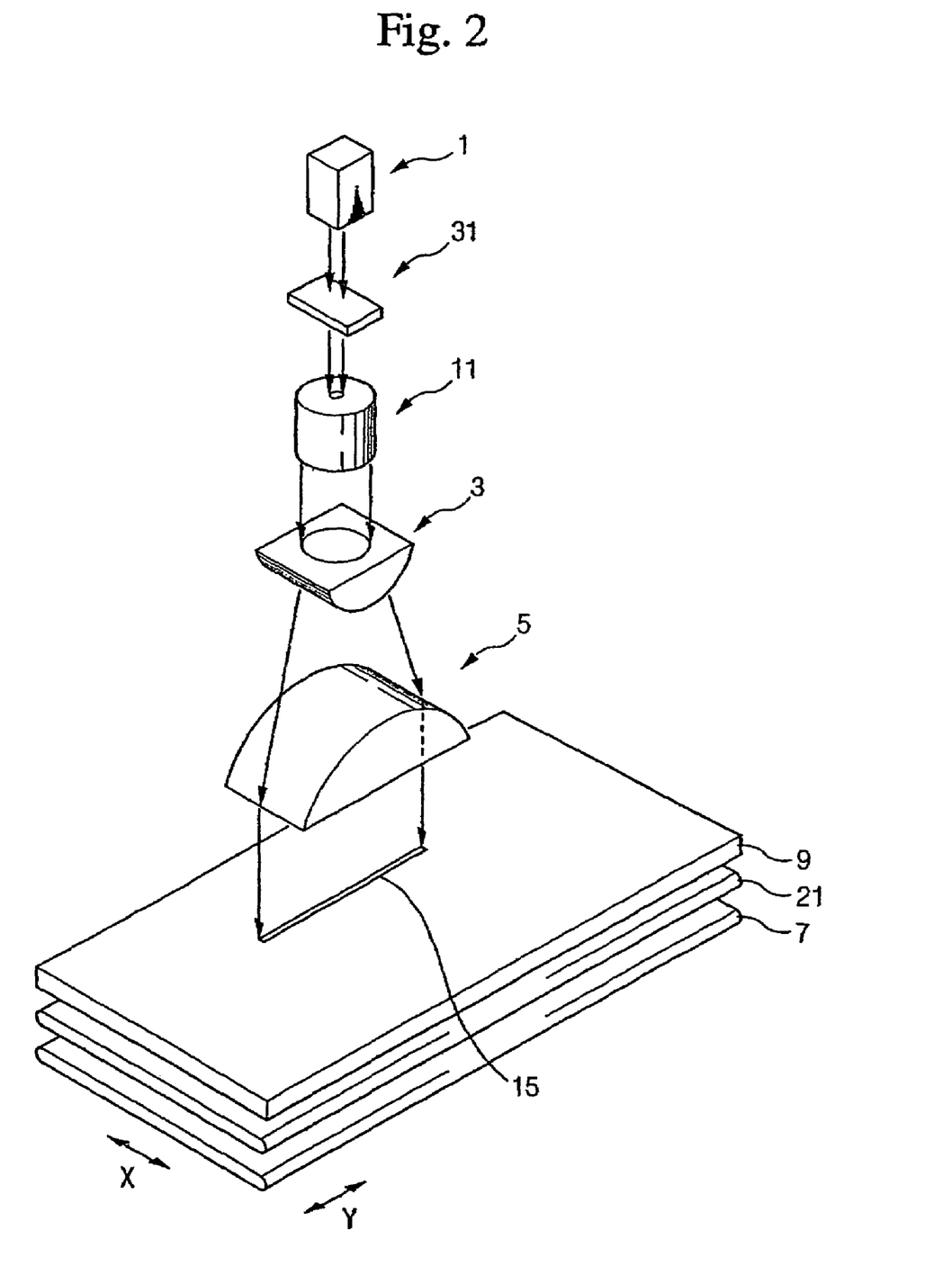
FIG. 2 is a perspective view illustrating an optical system of the transmittance-type glass substrate test apparatus according to a first embodiment of the present invention.

The beam shaper 3 and the beam collimator 5 each have shapes of semi-circular cylinders and are arranged with any pair of convex—convex lenses, convex-concave lenses, concave-convex lenses, and concave—concave lenses. The beam shaper 3 and the beam collimator 5 can be used as a single pair as shown in FIG. 2, or in multiple pairs.

The laser beam from the beam expander 11 is spread by being passed through the beam shaper 3, such that the spread laser beam has an elongated or elliptical cross-section. The laser beam passed through the beam shaper 3 is no longer parallel and has different incident angles than the beam collimator 5. A plurality of beam shaper 3 can be arranged such that the shaped laser beams from the beam shaper 3 are partially overlapped or aligned without a distance therebetween.

The spread laser beam, with different incident angles in different parts, is then parallelized by passing through the beam collimator 5 so as to be transmitted through the surface of the glass substrate 9 at a vertical incident angle for measuring the double refraction.

Figure 3:
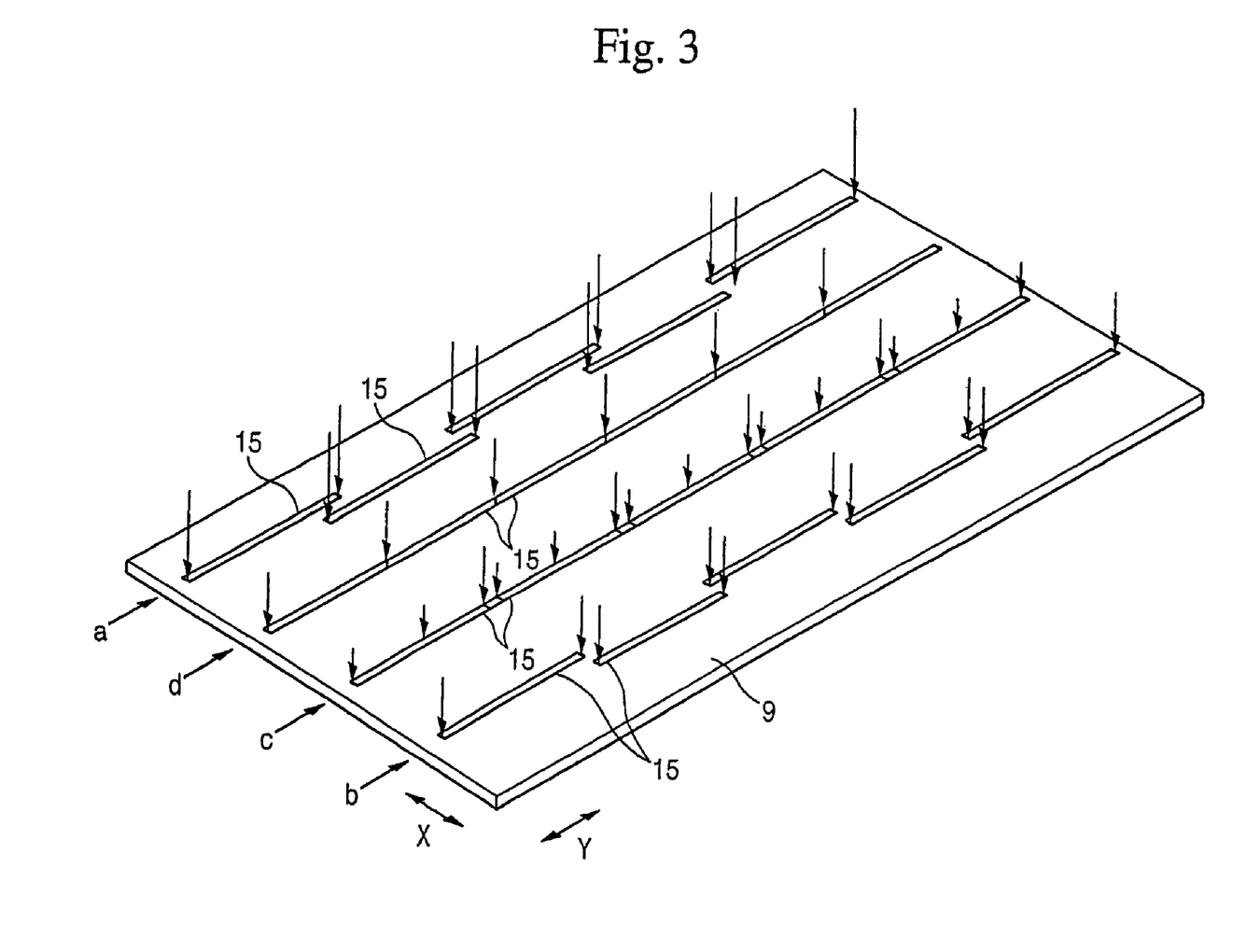
FIG. 3 is a perspective view for illustrating formations of inspection beams projected to the glass substrate.

As shown in FIG. 3, several pairs of beam shaper 3 and beam collimator 5 can be used for producing multiple inspection laser beams 15.

The beam shaper 3 and the beam collimator 5 can be configured in 4 formations so as to fit the inspection laser beam 15 to a size of the glass substrate.

The inspection beams are linearly arranged in a vertical direction (Y) relative to a direction (X) to which, the glass substrate progresses.

In a first formation (a), the inspection, beams are alternately arranged in two rows relative to a progression direction of the glass substrate so as to overlap each other for covering a width of the glass substrate 9. In a second formation (b), the inspection beams are alternately arranged in two rows without overlapping each other. In a third formation (c), the inspection beams are linearly arranged in one row such that the inspection beams in the same row partially overlap each other, while in the fourth formation (d), the inspection beams are linearly arranged in one row such that the ends of the inspection beams are aligned with each other.

These inspection beams transmit to the glass substrate and are then double-refracted through the alignment layer. The double refraction of the alignment layer varies according to a rubbing state and the anisotropy of the alignment layer material generated when curing the alignment layer, such that it is determined whether or not the glass substrate has defects by comparing the measured double refraction with the standard double refraction.

In FIG. 1, the photo detector 7 is arranged so as to detect the double refraction of the alignment layer while the shaped laser beam scans the whole surface of the glass substrate 9. The photo detector 7 can be constructed so as to detect the double refraction of the alignment per unit area by detecting the laser beam passing through the glass substrate, by constructing it as either a single or an array type identical to the glass substrate 9. The photo detector 7 covers the whole surface of the glass substrate 9 and performs image processing in units of pixels for measuring the double refraction.

In the case the photo detector 7 is structured as a single type, the photo detector 7 continuously scans the surface of the glass substrate 9 with a speed identical to the line speed, and in the case the photo detector is structured as an array type, the laser unit 1 and the photo detector 7 are fixedly installed so as to cover the whole surface of the glass substrate 9 such that the photo detector 7 measures the double refraction of the entire alignment layer at one time.

The double refraction detected by the photo detector 7 is compared with the standard laser double refraction by a phase detector 13 such that it is determined whether or not the measured double refraction is in the range of the standard double refraction, and the determination result is displayed on a monitor screen 17. The standard laser double refraction can be changed according to the device using the glass substrate.

Also, the polarizer 31 is arranged between the laser unit 1 and the beam shaper 3 or between the beam shaper 3 and the beam collimator 5 for polarizing the laser beam to a parallel ray.

The laser unit 1, beam expander 11, beam shaper 3, beam collimator 5, and the polarizer 31 can be integrated as an optical system (see FIG. 2). Also, the optical system can be integrally formed with the laser unit 1, the beam shaper 3, the beam collimator 5, and the polarizer 31, excepting the expander 11.

It is preferred that a plurality of optical systems are appropriately arranged in consideration of the size of the shaped laser beam and the size of the glass substrate 9, as shown in FIG. 1. In FIG. 1, each optical system includes a beam expander 11.

When measuring the laser double refraction in this manner, a sprayer 19 is arranged above the glass substrate 9 so as to spray alcohol or an organic compound for enhancing the laser double refraction.

Over the photo detector 7, i.e. between the glass substrate 9 and the photo detector 7, a polarization elastic modulator 21 is arranged so as to form a required wavelength of $\lambda/2$ or $\lambda/4$.

The glass substrate test apparatus of the present invention can be used together with a visual test device using any of ultraviolet, infrared, or visible rays for detecting foreign bodies on the surface of the glass substrate 9 in an LCD manufacturing line.

Figure 4:
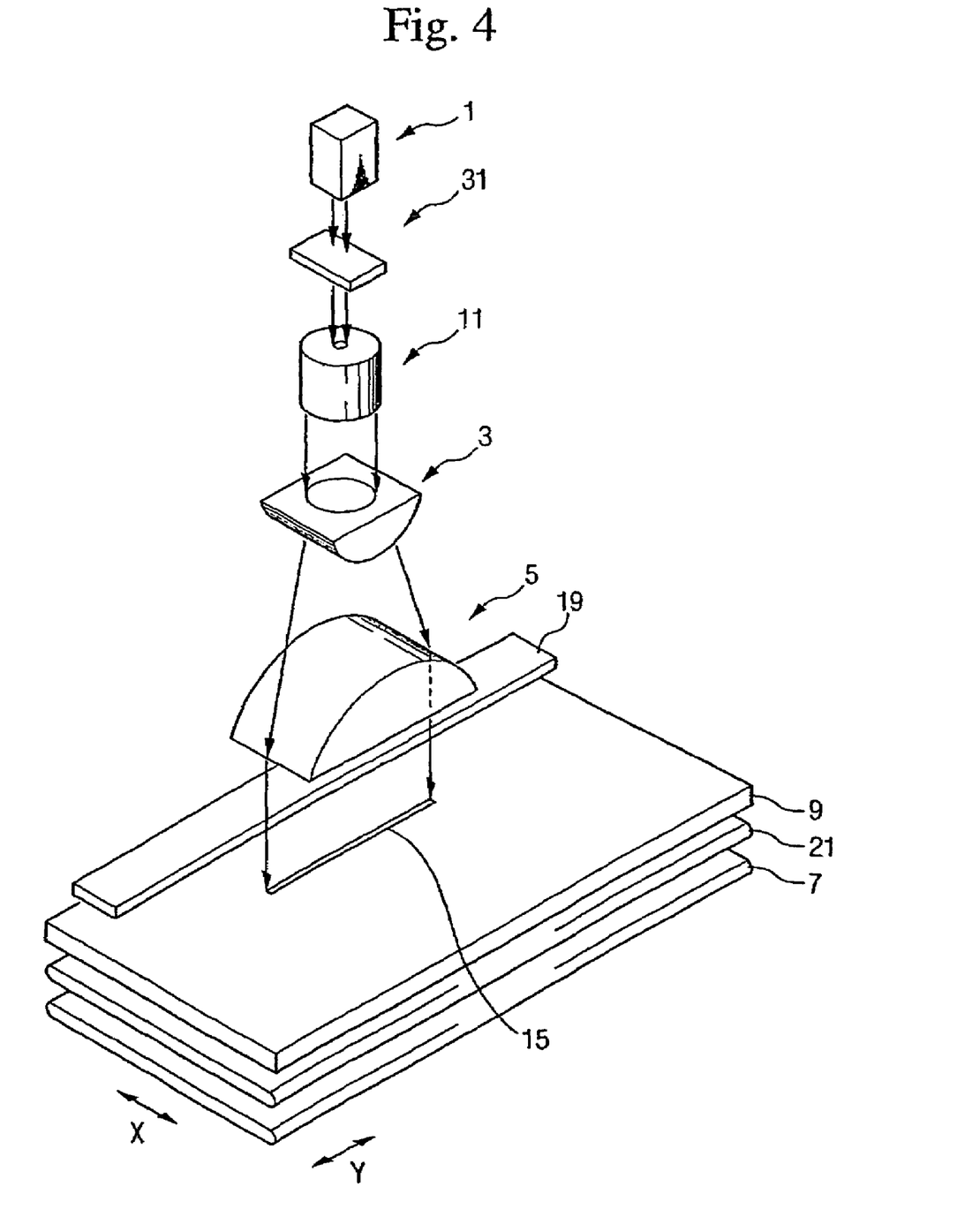
FIG. 4 is a perspective view illustrating an optical system of the transmittance-type glass substrate test apparatus according to a second embodiment of the present invention.

As shown in FIG. 2 to FIG. 4, the inspection laser beam 15 emitting to the surface of the glass substrate 8 has a shape of an elongated slit. For performing the inspection, it is possible to move the inspection laser beam 15 or the glass substrate 9, but it is preferable that the glass substrate moves in consideration of the manufacturing line characteristics.

Figure 5:
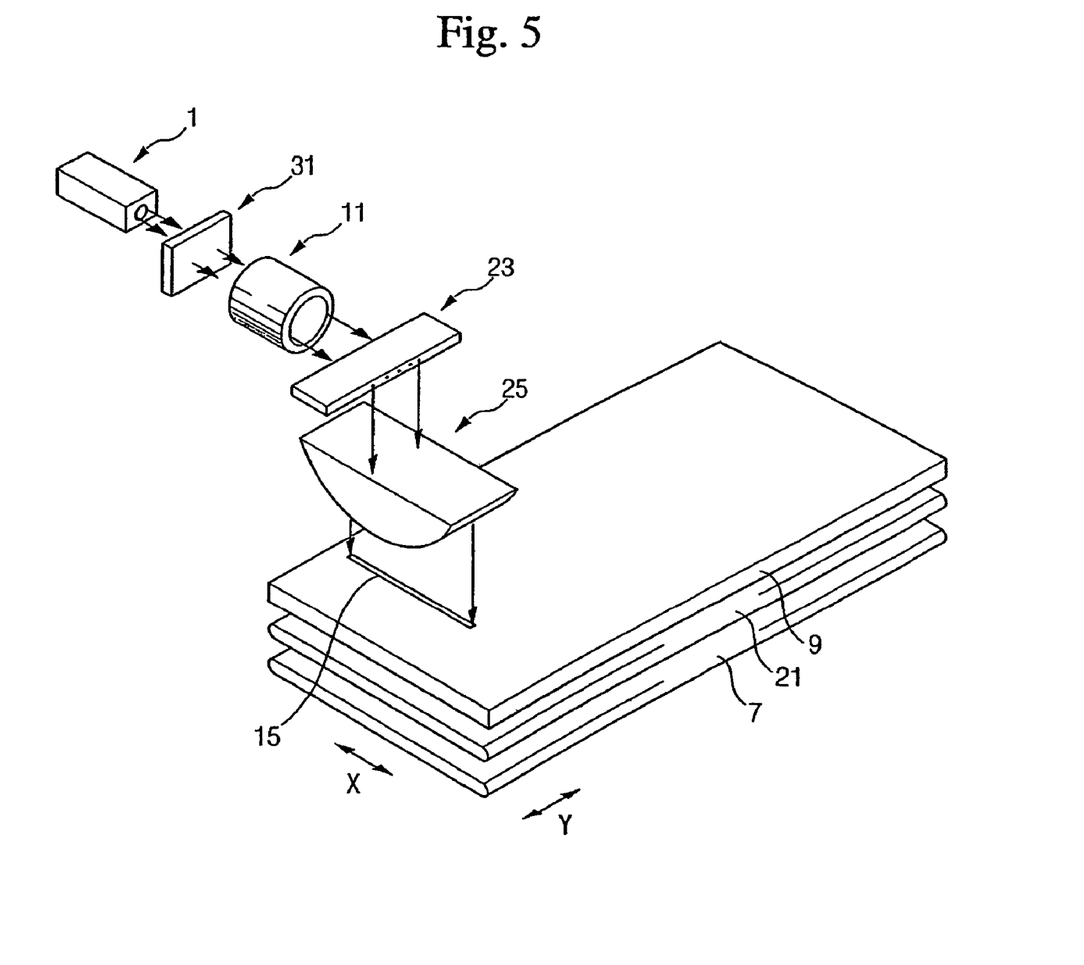
FIG. 5 is a perspective view illustrating an optical system of the transmittance-type glass substrate test apparatus according to a third embodiment of the present invention.

FIG. 5 is a perspective view of the optical system adopting a Galvano scanner 23 and an f-θ lens 25 instead of the beam shaper 3 and the beam collimator 5.

Since the structure and the operation of the optical system of FIG. 5 is similar to the optical system of FIG. 2, only the features of the optical system of FIG. 5 that are different from the optical system of FIG. 2 will be described.

The Galvano scanner 23 spreads the laser beam emitted from the laser unit 1 into multiple directions so as to make a cross section of the spread laser beam have an elongated slit shape, and the f-θ lens 25 paralyzes the spread laser beam.

The laser unit 1 can use any of He—Ne (632.8 nm wavelength), Ar, and $CO_2$ lasers having a single wavelength, or a cross Zeemann laser (He—Ne). In the case of using the cross Zeemann laser, among two laser beams f1 and f2 having a linear polarization characteristic, the first laser f1 is directed to the phase detector 13 for the purpose of reference and the second laser f2 is directed so as to pass through the Galvano scanner 23 and the f-θ lens 25. The second laser f2 refracts through the alignment layer so as to be detected by the photo detector 7, and the phase detector 13 detects the double refraction of the laser beam so as to display the result on the monitor screen 17.

In this case, the glass substrate 9 is mounted on a stage (not shown) that moves in the Y direction such that the photo detector 7 scans the glass substrate 9 while it is moving in the X direction for measuring the double refraction over the whole alignment layer formed on the glass substrate 9.

Figure 6:
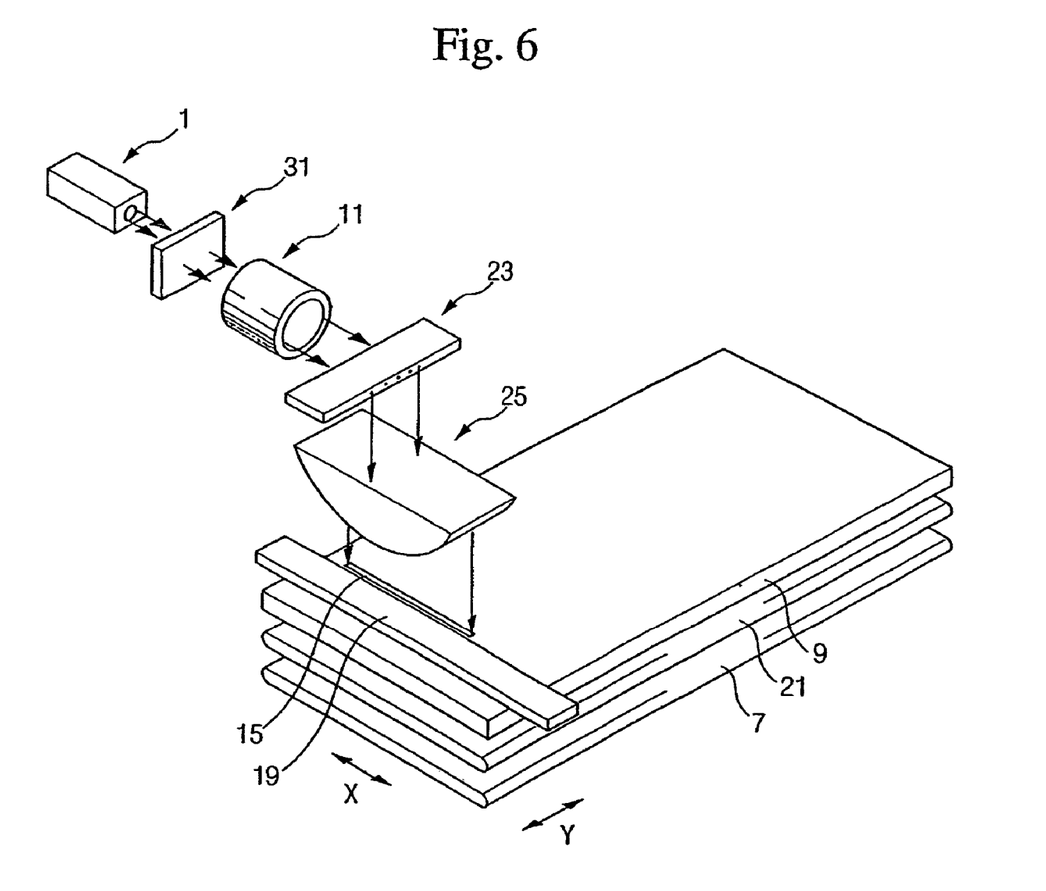
FIG. 6 is a perspective view illustrating an optical system of the transmittance-type glass substrate test apparatus according to a fourth embodiment of the present invention.

FIG. 6 shows the optical system having a sprayer 19. The sprayer 19 operates identically with the sprayer depicted in FIG. 1 and FIG. 4, so it will not be explained in detail.

Figure 7:
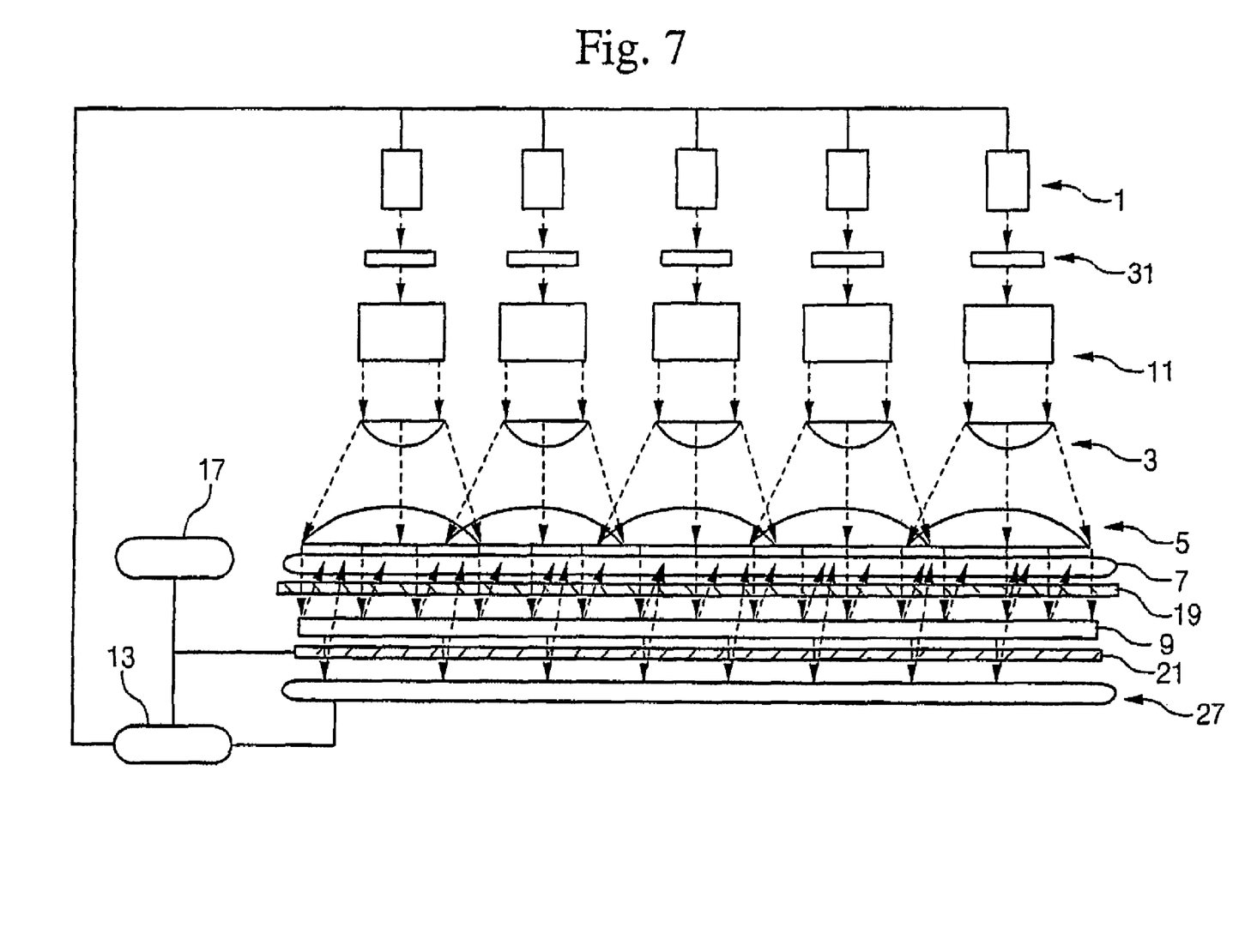
FIG. 7 is a block diagram showing a reflection-type glass substrate test apparatus according to the present invention.

FIG. 7 is a schematic diagram showing the glass substrate test apparatus of the present invention. Since the basic structure and operation of the glass substrate test apparatus is identical to that of the apparatus of FIG. 1 to FIG. 6, only different features will be described in detail.

Figure 8:
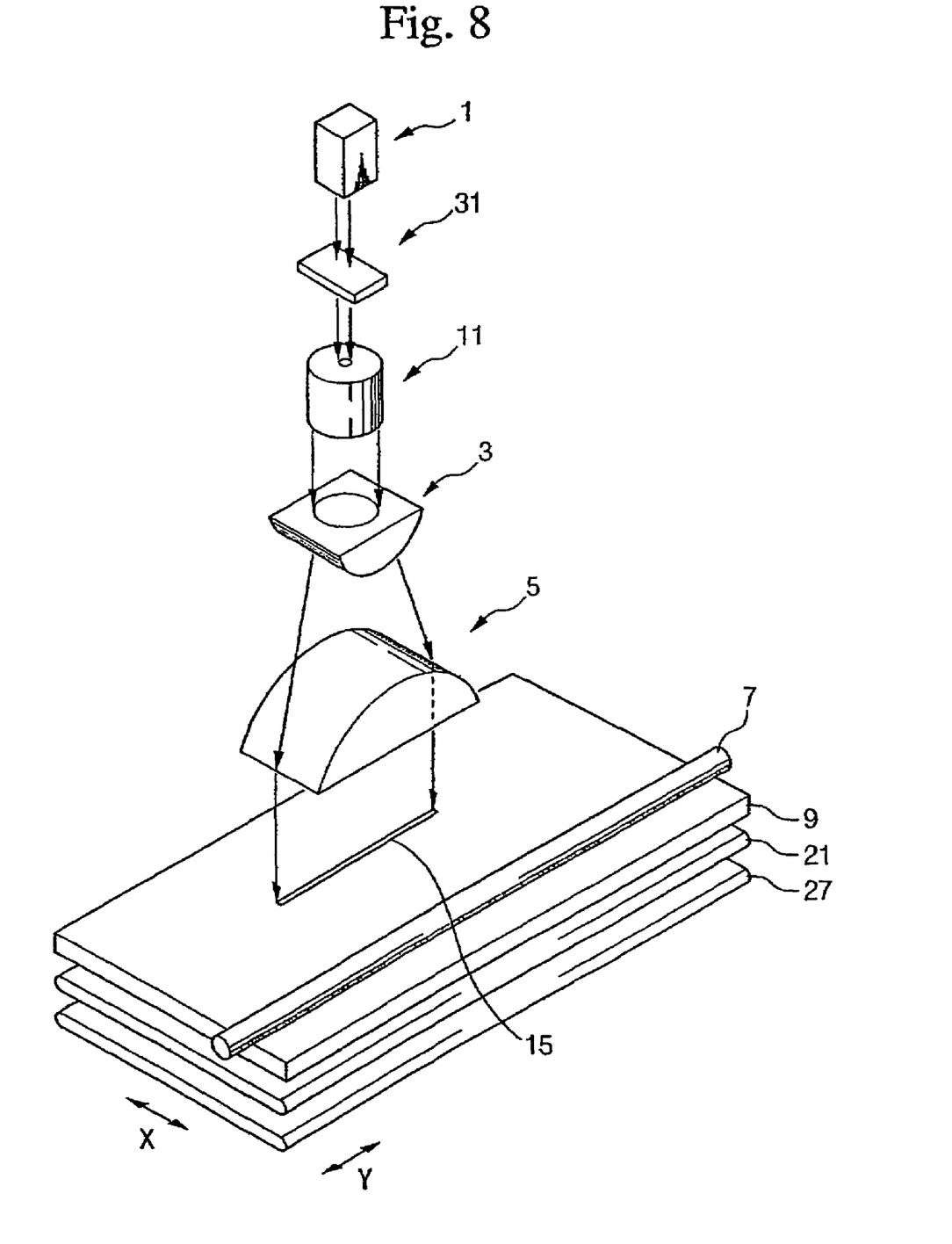
FIG. 8 is a perspective view illustrating an optical system of the reflection-type glass substrate test apparatus according to a fifth embodiment of the present invention.

FIG. 8 shows an optical system of, the glass substrate test apparatus of FIG. 7.

In the case a metal electrode or color filter resin blocks the penetration of the laser beam on the TFT and pixels of the color filter during the glass substrate test, a resolving power of the photo detector 7 reduces due to a lack of refraction amount of the laser beam 15. To solve this problem, a reflection-type glass substrate test apparatus is used.

In the penetration-type glass substrate test apparatus depicted in FIG. 1 to FIG. 6, the laser beam is projected from above the glass substrate 9 and the photo detector 7, arranged below the glass substrate 9, detects the double refraction of the transmitted laser beam.

On the other hand, in the reflection-type glass substrate test apparatus depicted in FIG. 7 to FIG. 9, the photo detector 7 is arranged above the glass substrate 9 and a reflection plate is arranged below the glass substrate 9 such that the laser beam transmitted to the glass substrate 9 is reflected by the reflection plate 27 so as to direct it to the photo detector 7. Accordingly, the reflected laser beam re-transmits through the glass substrate 9 such that the photo detector 7 measures the double refraction of the laser beam.

It is preferable that the reflection plate 27 is made of a metallic material such as Al, Cr, Ni, etc., or nonmetallic material such as Si.

Figure 9:
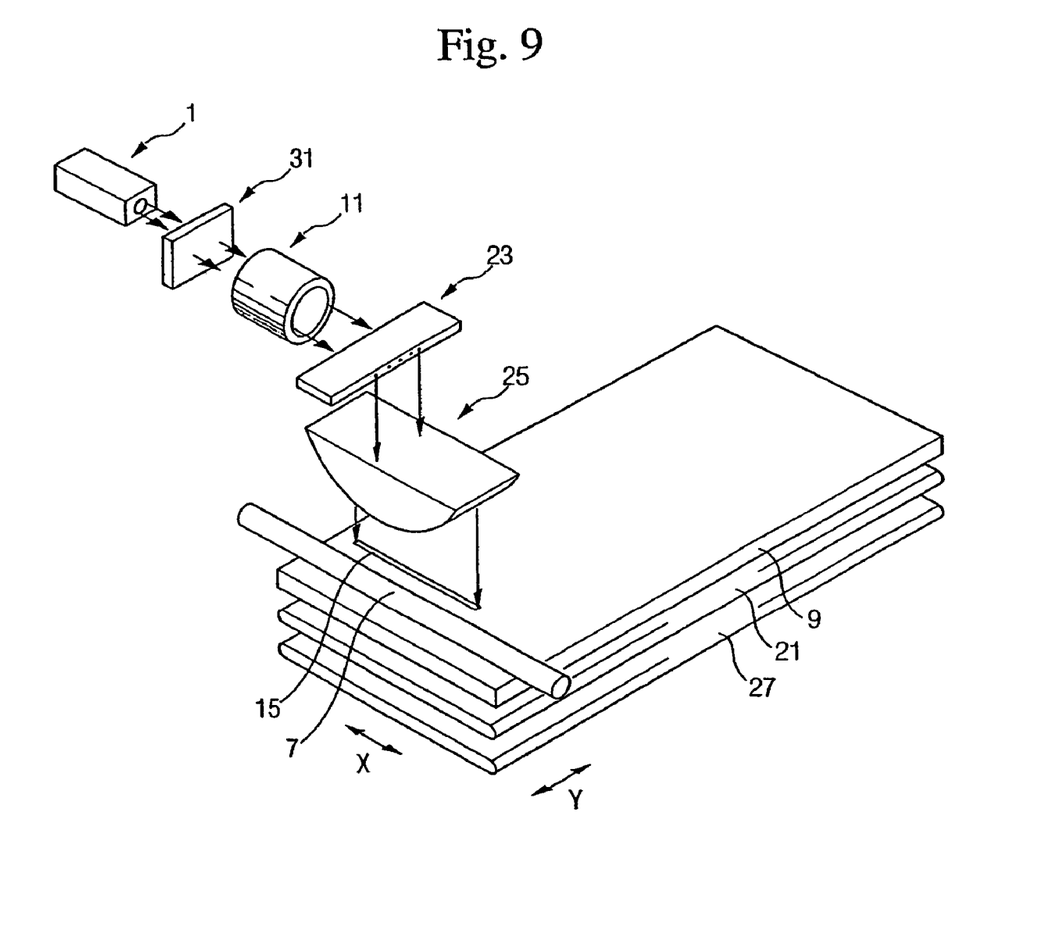
FIG. 9 is a perspective view illustrating an optical system of the reflection-type glass substrate test apparatus according to a sixth embodiment of the present invention.

FIG. 9 shows a reflection-type glass substrate test apparatus adopting the optical system of FIG. 5. The method of measuring the double refraction of the laser beam in this apparatus is identical with that of the apparatus depicted in FIG. 7 and FIG. 8, and the operations of the Galvano scanner 23 and the f-θ lens 25 are identical with the those explained with respect to FIG. 5, and operations of the same elements will not be explained.

The size of the reflection plate 27 can be equal to or greater than the size of the glass substrate 9, and it can have the shape of a slit identical to the shape of the cross section of the inspection laser beam 15. Also, the photo detector 7, arranged above the glass substrate 9, can be structured such that the coverage area is equal to or greater than the size of the glass substrate 9, and it can have the shape of a slit identical to the shape of the cross section of the inspection laser beam 15. The reflection plate 27 is equal to the glass substrate 9 in size, and the photo detector 7 has the shape of the slit that is identical to the cross section of the inspection laser beam 15 in this embodiment.

Figure 10:
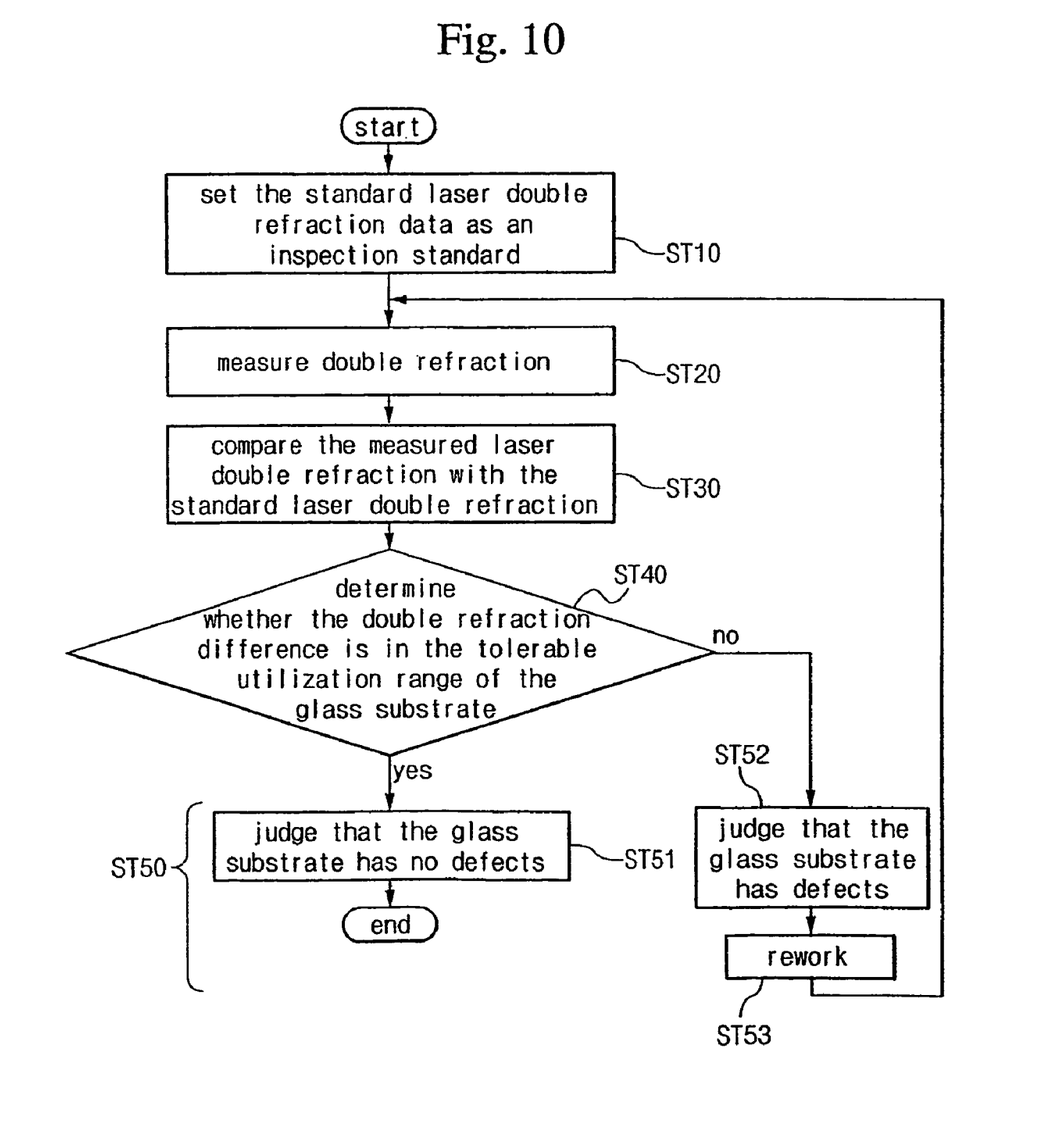
FIG. 10 is a flow chart for illustrating the glass substrate test method of the present invention.

The operation of the glass substrate test apparatus structured as above will be described hereinafter, with reference to FIG. 10.

Firstly, the standard laser double refraction data is set as an inspection standard at step ST10. The standard laser double refraction value is a double refraction value of the laser beam transmitted through the glass substrate 9 that is within the utilization range of the glass substrate 9.

The glass substrate test apparatus measures the double refraction by projecting the laser beam over the whole surface of the glass substrate 9 at step ST20. In this case, the inspection can be performed in such a manner that the glass substrate passes under the fixed inspection laser beam according to the speed of the LCD manufacturing line, or the inspection laser beam scans the whole of the surface of the glass substrate when the glass substrate stops moving under the inspection laser beam.

The glass substrate test apparatus compares the measured laser double refraction with the standard laser double refraction at step ST30, and determines whether or not the double refraction difference is in the tolerable utilization range of the glass substrate 9 at step ST40.

The glass substrate test apparatus judges that the glass substrate has no defects and ends the inspection at step ST51 if the double refraction difference is within the tolerable utilization range of the glass substrate 9, and the glass substrate test apparatus judges that the glass substrate 9 has defects at step ST52 if the double refraction difference is outside the tolerable utilization range of the glass substrate 9 such that the glass substrate 9 is reworked at step ST53 and then re-inspected at step ST50.

Now, the principle for detecting defects on the glass substrate using the laser double refraction adapted to the glass substrate test method will be described.

If one of two rays picks up information, this information is reflected to an optical beat. In this case, the information is a signal of the amplitude, phase, and frequency of the ray. That is, in the case information exists in the ray, another ray (a reference ray) is amalgamated with the ray such that the information can be obtained from the optical beat. This is called optical heterodyne interferometry.

In the case of using an amplifier for detecting the signal, optical heterodyne interferometry has advantages in that it is possible to perform a highly precise and sensitive measurement, the signal ray is not effected by disturbance when the signal only has phase information and by other frequency components, and it is possible to detect a weak signal by amplifying the intensity of the reference ray.

Optical heterodyne interferometry can be explained using the following equations. Electric field components of respective reference and signal rays are expressed by Er and Es.

$$Er = a_r \cos(2\pi f_r t + \phi_r) \qquad \text{<equation 1>}$$

$$Er = a_s \cos(2\pi f_s t + \phi_s) \qquad \text{<equation 2>}$$

where $a_r$ and $a_s$ are amplitudes of respective reference and signal rays, $f_r$ and $f_s$ are frequencies of respective reference and signal rays, and $\phi_r$ and $\phi_s$ are phases of the respective reference and signal rays.

An intensity "I" of the detected ray, when the two rays are amalgamated, can be expressed by the following equation 3.

$$I = |Es + Er|^2$$
$$= \frac{\alpha_s^2 + \alpha_r^2}{2} + 2\alpha_s\alpha_r\cos(2\pi(f_s - f_r)t + (\Phi_s - \Phi_r))$$
$$= \frac{\alpha_s^2 + \alpha_r^2}{2} + 2\alpha_s\alpha_r\cos(2\pi f_b t + \Delta)$$

where t is an average time, $f_b$ is a frequency of the optical beat, and $\Delta$ is a phase difference of the two optical components.

An optical current detected by the photo detector 7 is comprised of direct current components corresponding to first and second terms, and an alternating current having a frequency ($f_b$) corresponding to the third term in equation 3. This alternating current is called the optical beat signal in optical heterodyne interferometry, the amplitude ($2a_s a_r$), frequency (9 $f_b$), or phase ($\Delta$) of the optical beat signal is measured so as to extract information included in the amplitude ($a_s$), frequency ($f_s$), or phase ($\phi_s$) or the optical signal.

The double refraction measurement using the optical heterodyne interferometry will be described hereinafter.

Consider penetrating a stabilized transverse Zeemann laser (STZL) through a sample having a double refraction property while the primary axis of the sample is identical with the surface of the polarization surface. When respective polarization components pass through the sample, the progress speed differs in a direction of the lead axis or a lag axis such that a phase difference is generated after passing through the sample. Accordingly, the double refraction amount of the sample can be precisely measured by detecting the phase difference using optical heterodyne interferometry.

Now, the principle of the double refraction measurement will be briefly described. A straight polarizer is used by interfering two rays. In this formation, the double refraction measurement can be performed with the precision of the electric phase detector. Since the precision of the electric phase detector is greater than 0.1 degree, the double refraction amount can be very precisely measured, to, the extent of {fraction (1/4000)} of the optical wavelength.

If refractive indexes of the sample are $n_x$ and $n_y$ and the width of the ray is d, phase delays $\phi_x$ and $\phi_y$ of the rays can be calculated with the following equation 4 and equation 5.

$$\Phi_x = \frac{2\pi n_x d}{\lambda} \qquad <\text{equation 4}>$$

$$\Phi_y = \frac{2\pi n_y d}{\lambda} \qquad <\text{equation 5}>$$

If the STZL oscillation ray transmits the sample, the optical intensity I detected by the photo detector can be expressed as the following equation 6.

$$I = |Ex + Ey|^2 \qquad <\text{equation 6}>$$
$$= \frac{\alpha_x^2 + \alpha_y^2}{2} + 2\alpha_x\alpha_y\cos(2\pi(f_x - f_y)t + (\Phi_x - \Phi_y))$$
$$= \frac{\alpha_x^2 + \alpha_y^2}{2} + 2\alpha_x\alpha_y\cos(2\pi f_b t + \Delta)$$
$$= \frac{\alpha_x^2 + \alpha_y^2}{2} + 2\alpha_x\alpha_y\cos\left(2\pi f_b t + \frac{2\pi(n_x - n_y)d}{2}\right)$$
$$= \frac{\alpha_x^2 + \alpha_y^2}{2} + 2\alpha_x\alpha_y\cos\left(2\pi\left(f_b t + \frac{\delta n d}{\lambda}\right)\right)$$

where $\Delta$ is a phase difference of the two optical components, and dn is a refraction index, i.e., the refraction amount. In equation 6, the phase difference of the two rays varies according to the phase difference of the beat signal difference. In this way, the refraction amount can be measured by measuring the phase of the optical beat signal using the electric phase detector.

Double refraction using the Zeemann laser will be described hereinafter.

Is this measurement method, two different wavelengths, such as 632 nm and 631 nm, are used for measuring the double refraction.

The two components are obtained on the same optical axis without adjustment, and the two components do not deviate from each other as a result of exterior effects such as temperature. The laser having a stable optical frequency is used. This laser obtains anisotropy in an oscillator by applying a He—Ne laser electric field, and it oscillates two polarization components having different frequencies. The Zeemann laser can be classified into horizontal and vertical lasers according to the direction of the magnetic field applied relative to the optical axis of the laser.

The horizontal laser is obtained by applying the magnetic field (horizontal magnetic field) in a direction perpendicular to the optical axis of the laser. If the horizontal magnetic field is applied to the He—Ne laser, two linear polarized components having different frequencies and being orthogonal to each other are oscillated. An intensity of the magnetic field applied to a laser tube is determined according to the length of the laser tube. The frequency difference of the two polarized components of the horizontal Zeemann laser is about a few dozen to a few hundred Kh such that the optical beat signal can be measured by electro-optic detection.

If the laser tube is temperature-stabilized, an optical frequency stability of $10^{-9}$ about $10^{-10}$ is obtained. This is called a stabilized transverse Zeemann laser.

The double refraction measurement data of the alignment layer according to the rubbing conditions is as follows.

The laser used in the method is a He—Ne laser having an oscillation wavelength of 832.8 nm. Four samples are tested, i.e., a single rubbing with a 60 Å rubbing depth, a double rubbing with a 120 Å rubbing depth, non-rubbing, and a glass (borosilicate glass) having no alignment layer. The double refraction can be calculated as follows.

$$\Delta = \sin\Gamma \sin 2\delta$$

$$\Gamma = \frac{2\pi \Delta n d}{\lambda}$$

$$\Delta n = \frac{\lambda}{2\pi d}\arcsin\frac{\Delta I}{\sin 2\delta}$$

where Γ is the phase delayed while passing the sample, d is a rotation angle ($10^5$), and d is the rubbing depth.

The double refractions measured with the respective samples are as follows.

Δn=$1.600 \times 10^{-2}$: double-rubbing alignment layer
Δn=$4.542 \times 10^{-3}$: single-rubbing alignment layer
Δn=$2.217 \times 10^{-8}$: non-rubbing alignment layer
Δn=$1.334 \times 10^{-7}$: glass having no alignment layer Referring to these data, the double refractions of samples differ from each other according to the conditions of the alignment layers such that the defects on the alignment layer can be inspected on the basis of these data.

Accordingly, the double refraction of the glass substrate (9), through which the shaped laser beam passes, is analyzed using a predetermined algorithm so as to be collected as the data.

That is, a normal double refraction of the alignment layer rubbed and dried under ideal conditions is stored as the standard double refraction, and this standard double refraction data is associated with the uniformity of the alignment layer such that whether or not the alignment layer has defects is determined by comparing the measured double refraction with a tolerable range of the standard double refraction. If the measured double refraction is outside the tolerable standard double refraction range, it is determined that the glass substrate has defects.

Figure 11:
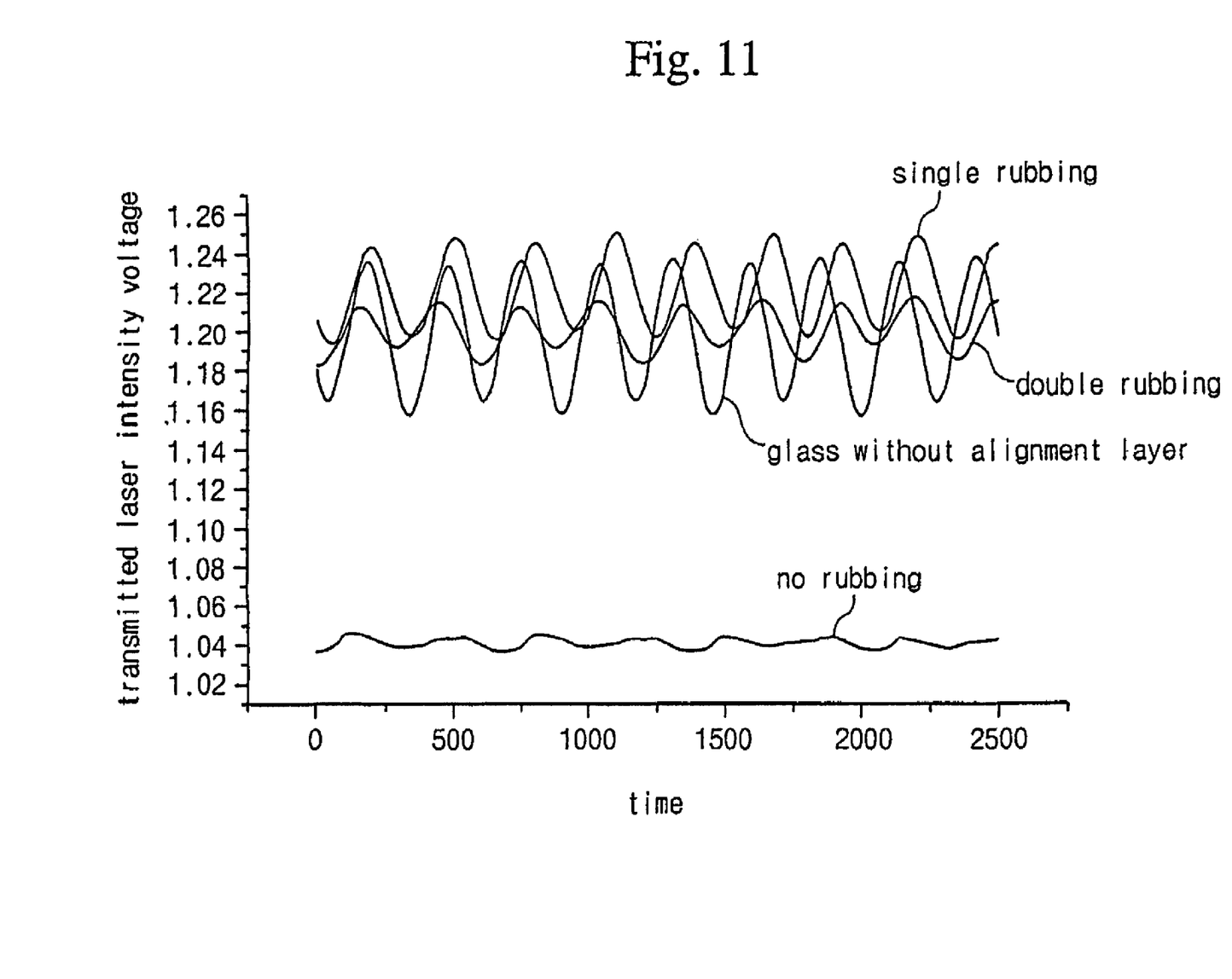
FIG. 11 is a graph for illustrating double refraction data on the samples.

FIG. 11 is a graph for illustrating transmitted laser intensity voltage per unit area according to the laser double refraction on the surface of the alignment layers having different rubbing conditions.

As described above, in the glass substrate test apparatus and method of the present invention, the laser beam emitted from the laser unit is shaped while passing through the beam shaper and the beam collimator, the shaped beam is projected to the surface of the glass substrate, a double-refraction of the laser transmitted over the glass substrate is measured by the photo detector, and the measured double refraction is compared with the standard laser double refraction so as to determine whether or not the glass substrate has defects. Accordingly, it is possible to inspect for defects on the glass substrate immediately after the drying and rubbing of the alignment layer on the glass substrate such that rework can be performed before charging the cell with the liquid crystal, resulting in LCD-manufacturing process enhancement and securing a 100% yield.

What is claimed is:

1. A glass substrate test apparatus in an LCD-manufacturing line comprising:
   a laser unit generating and emitting a laser beam;
   a beam shaper for shaping the laser beam so that said laser beam has an elongated or elliptical cross-section from the laser unit and a beam collimator for collimating the laser beam from the beam shaper;
   a photo detector for measuring double refraction intensity of a whole surface of a glass substrate using a split laser beam from the beam collimator;
   a phase detector for comparing a laser double refraction measured by the photo detector with a standard laser double refraction; and
   a polarizer arranged between the laser unit and the beam shaper or between the beam shaper and the beam collimator for polarizing the laser beam.

2. The glass, substrate test apparatus of claim 1, wherein the beam shaper and the beam collimator are formed in one of 4 configurations, which are convex—convex lens, convex-concave lens, concave-convex lens, and concave—concave lens configurations.

3. The glass substrate test apparatus of claim 1, wherein a plurality of beam shapers and beam collimators are used for covering a width of the whole glass substrate, and the laser beams and the parallel laser beam shapers are arranged such that the laser beams are alternately arranged In two rows relative to a progression direction of the glass substrate having a distance between the split laser beams in the same row.

4. The glass substrate test apparatus of claim 3, wherein the split laser beams are arranged such that the split laser beams are overlapped in two other rows over a predetermined length.

5. The glass substrate test apparatus of claim 1, wherein a plurality of beam shapers and beam collimators are used for covering a width of the whole glass substrate, and the laser beam shapers and the beam collimaters are arranged such that the laser beams are arranged in a single row.

6. The glass substrate test apparatus of claim 5, wherein the split laser beams are arranged such that the split laser beams are overlapped over a predetermined length.

7. The glass substrate test apparatus of claim 1, wherein the laser unit, the beam shaper, the beam collimator, and the polarizer are configured in an integral optical system such that the plurality of optical systems are used in consideration of a size of the glass substrate and a length of a split laser beam.

8. The glass substrate test apparatus of claim 1, wherein the photo detector is arranged as a single or an array type identical with the glass substrate for detecting the laser double refraction per unit area.

9. The glass substrate test apparatus of claim 1, further comprising a beam expander arranged between the laser unit and the beam shaper for expanding the laser beam emitted from the laser unit.

10. A glass substrate test apparatus in an LCD-manufacturing line comprising:
    a laser unit generating and emitting a laser beam;
    a beam shaper for splitting the laser beam from the laser unit and a beam collimator for parallelizing the laser beam from the beam shaper;
    a photo detector for measuring double refraction intensity of a whole surface of a glass substrate using a split laser beam from the beam collimator;
    a phase detector for comparing a laser double refraction measured by the photo detector with a standard laser double refraction;
    a polarizer arranged between the laser unit and the beam shaper or between the beam shaper and the beam collimator for polarizing the laser beam; and
    a sprayer arranged between the beam collimator and the glass substrate for magnifying the laser double refraction by spraying water, alcohol, or an organic compound on the glass substrate.

11. A glass substrate test apparatus in an LCD-manufacturing line comprising:
    a laser unit generating and emitting a laser beam;
    a beam shaper for splitting the laser beam from the laser unit and a beam collimator for parallelizing the laser beam from the beam shaper;
    a photo detector for measuring double refraction intensity of a whole surface of a glass substrate using a split laser beam from the beam collimator;
    a phase detector for comparing a laser double refraction measured by the photo detector with a standard laser double refraction;

a polarizer arranged between the laser unit and the beam shaper or between the beam shaper and the beam collimator for polarizing the laser beam; and a polarization elastic modulator arranged between the glass substrate and the photo detector for forming a required wavelength.

12. The glass substrate test apparatus of claim 1, wherein the laser unit is arranged above the glass substrate and the photo detector is arranged below the glass substrate for detecting double is refraction of the laser transmitted over the glass substrate.

13. The glass substrate test apparatus of claim 1, further comprising a reflection plate arranged below the glass substrate for reflecting the laser transmitted through the glass substrate wherein the laser unit and the photo detector are arranged above the glass substrate for detecting the double refractions of the laser beam reflected through the glass substrate by the reflection plate.

14. A glass substrate test method in a liquid crystal cell fabricating process comprising:

setting standard laser double refraction data to a inspection standard;

detecting laser double refraction by projecting a laser beam over a whole glass substrate;

comparing the detected laser double refraction with the standard laser double refraction;

determining whether or not a double refraction difference is within a utilization range of the glass substrate; and judging that the glass substrate has no defects if the double refraction difference is within the utilization range of the glass substrate, or judging that the glass substrate has defects if the double refraction difference is outside the utilization range of the glass substrate and then reworking the glass substrate.

15. A glass substrate test method in a liquid crystal cell fabricating process comprising:

setting standard laser double refraction data to a inspection standard;

detecting laser double refraction by projecting a laser beam over a whole glass substrate;

comparing the detected laser double refraction with the standard laser double refraction;

determining whether or not a double refraction difference is within a utilization range of the glass substrate; and judging that the glass substrate has no defects if the double refraction difference is within the utilization range of the glass substrate, or judging that the glass substrate has defects if the double refraction difference is outside the utilization range of the glass substrate and then reworking the glass substrate;

wherein while detecting the laser double refraction, the glass substrate to be tested moves at a speed of a liquid crystal cell process line below a inspection laser beam.

16. The glass substrate test method of claim 14, wherein while detecting the laser double refraction, the glass substrate to be tested is positioned below an inspection laser beam without moving.

17. The glass substrate test apparatus of claim 1 further comprising a glass substrate, wherein the laser beam exiting the beam collimator reaches the glass substrate in a non-Gaussian distribution state.

* * * * *